(12) United States Patent
Uridil et al.

(10) Patent No.: US 11,766,552 B2
(45) Date of Patent: Sep. 26, 2023

(54) CONDUIT CONNECTORS AND FLUID ASSEMBLIES FOR ENTERAL FEED PUMPS, AND METHODS THEREOF

(71) Applicant: Medline industries, LP, Northfield, IL (US)

(72) Inventors: Morgan Uridil, Evanston, IL (US); Michael V. Turturro, Arlington Heights, IL (US); Bahram Kevin Kayvani, Chicago, IL (US); Douglas Komandt, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 646 days.

(21) Appl. No.: 16/943,654

(22) Filed: Jul. 30, 2020

(65) Prior Publication Data
US 2022/0032030 A1    Feb. 3, 2022

(51) Int. Cl.
| | | |
|---|---|---|
| *A61M 1/06* | (2006.01) | |
| *A61M 39/12* | (2006.01) | |
| *A61J 15/00* | (2006.01) | |

(52) U.S. Cl.
CPC .......... *A61M 39/12* (2013.01); *A61J 15/0076* (2015.05)

(58) Field of Classification Search
CPC .... A61J 15/0076; A61J 5/0026; A61M 5/142; A61M 39/12; A61M 3/027
See application file for complete search history.

(56) References Cited

U.S. PATENT DOCUMENTS

| | | | |
|---|---|---|---|
| 2,236,802 A | | 4/1941 | McDonald |
| 3,169,528 A | | 2/1965 | Knox, III |
| 3,558,163 A | * | 1/1971 | Moore et al. ....... F16L 27/0845 285/321 |
| 4,405,316 A | * | 9/1983 | Mittleman ............ A61M 39/04 604/86 |
| 4,585,399 A | | 4/1986 | Baier |
| 4,804,206 A | * | 2/1989 | Wood .................. F16L 27/0841 285/321 |

(Continued)

FOREIGN PATENT DOCUMENTS

| | | |
|---|---|---|
| CN | 303793606 | 8/2016 |
| EP | 0074632600005 | 3/2020 |

(Continued)

OTHER PUBLICATIONS

DFC—Double-wall Flexible Gas Vent Connector, Hart Cooley, [Post date: May 18, 2013], [Site seen: Apr. 21, 2022], Seen at URL: https://www.hartandcooley.com/products/dfc/double-wall-flexible-gas-vent-connector (Year: 2013); 2 pages.

(Continued)

*Primary Examiner* — Rebecca E Eisenberg
(74) *Attorney, Agent, or Firm* — Fitch, Even, Tabin & Flannery LLP

(57) ABSTRACT

A conduit connector for an enteral feeding pump includes a fluid inlet portion that has an inlet axis and a fluid outlet portion that has an outlet axis that is parallel to and laterally offset from the inlet axis. The fluid inlet portion defines an elongated side slot extending parallel to the inlet axis for receiving tubing therethrough. The conduit connector further includes a bridge portion that extends between and connects the fluid inlet portion and the fluid outlet portion.

21 Claims, 9 Drawing Sheets

(56) References Cited

U.S. PATENT DOCUMENTS

| | | | |
|---|---|---|---|
| 5,057,076 A | 10/1991 | Polaschegg |
| 5,201,711 A | 4/1993 | Pasqualucci |
| 5,213,483 A | 5/1993 | Flaherty |
| 5,242,279 A | 9/1993 | Knuth |
| 5,312,334 A | 5/1994 | Hara |
| D348,097 S | 6/1994 | Inda |
| 5,569,026 A | 10/1996 | Novak |
| 5,772,255 A | 6/1998 | Osborne |
| 5,876,371 A | 3/1999 | Yokoyama |
| D488,545 S | 4/2004 | Takamatu |
| 7,462,170 B2 | 12/2008 | Fournie |
| 7,722,562 B2 | 5/2010 | Hanlon |
| 7,722,573 B2 | 5/2010 | Harr |
| 7,753,881 B2 | 7/2010 | Fournie |
| 7,753,883 B2 | 7/2010 | Fournie |
| 7,758,551 B2 | 7/2010 | Wiesner |
| 7,763,005 B2 | 7/2010 | Knauper |
| D625,805 S | 10/2010 | Hereford |
| 7,846,131 B2 | 12/2010 | Hudson |
| 7,927,304 B2 | 4/2011 | Hudson |
| 8,034,028 B2 | 10/2011 | Fournie |
| 8,052,642 B2 | 11/2011 | Harr |
| 8,052,643 B2 | 11/2011 | Hudson |
| 8,142,399 B2 | 3/2012 | Hanlon |
| 8,142,404 B2 | 3/2012 | Knauper |
| 8,361,024 B2 | 1/2013 | Fournie |
| D676,941 S | 2/2013 | Kluss |
| 9,192,709 B2 | 11/2015 | Francesco |
| 9,402,789 B2 | 8/2016 | Knauper |
| 9,468,714 B2 | 10/2016 | Butterfield |
| D783,784 S | 4/2017 | Bates-Hurtado |
| D783,786 S | 4/2017 | Madireddi |
| D799,638 S | 10/2017 | Janton |
| 9,814,819 B2 | 11/2017 | Concepcion |
| D866,748 S | 11/2019 | Khabiri |
| 10,518,015 B2 | 12/2019 | Concepcion |
| 10,596,532 B2 | 3/2020 | Lee |
| D920,504 S | 5/2021 | Bauer |
| 11,185,646 B2 | 11/2021 | Salegui Echeveste |
| 2003/0212381 A1 | 11/2003 | Whitehead, III |
| 2005/0165304 A1 | 7/2005 | Albertelli |
| 2009/0139530 A1 | 6/2009 | Landis |
| 2009/0214365 A1 | 8/2009 | Norman |
| 2011/0004143 A1 | 1/2011 | Beiriger |
| 2011/0315611 A1 | 12/2011 | Fulkerson |
| 2015/0021909 A1 | 1/2015 | Gulliver |
| 2016/0121096 A1 | 5/2016 | Rotem |
| 2016/0235938 A1 | 8/2016 | Khabiri |
| 2018/0056024 A1 | 3/2018 | Harrington |
| 2018/0133667 A1 | 5/2018 | Lee |
| 2018/0207389 A1 | 7/2018 | Fyfe |
| 2020/0000682 A1 | 1/2020 | Hoffstetter |
| 2020/0018306 A1 | 1/2020 | Leach |
| 2020/0054823 A1 | 2/2020 | Baier |
| 2020/0085695 A1 * | 3/2020 | O'Keefe ............ A61J 15/0053 |
| 2020/0179592 A1 | 6/2020 | Adams |
| 2021/0316106 A1 | 10/2021 | Canady |

FOREIGN PATENT DOCUMENTS

| | | |
|---|---|---|
| EP | 0084113340004 | 2/2021 |
| GB | 6114358 | 1/2021 |
| KR | 1020130099127 | 9/2013 |
| WO | 2011008624 | 1/2011 |

OTHER PUBLICATIONS

Vyaire Medical 3215, Airlife® Connector, 1/EA (243789_EA) 32151900, Air Life, Clean it Supply.com, [Post Date: unknown], [Site seen Apr. 21, 2022], Seen at URL: https://www.cleanitsupply.com/p-134650/vyaire-medical-3215-airlife-connector-1-ea-243789_ea-32151900.aspx (Year: 2022).

International Search Report and Written Opinion for International Application No. PCT/US21/41373 dated Nov. 1, 2021.

* cited by examiner

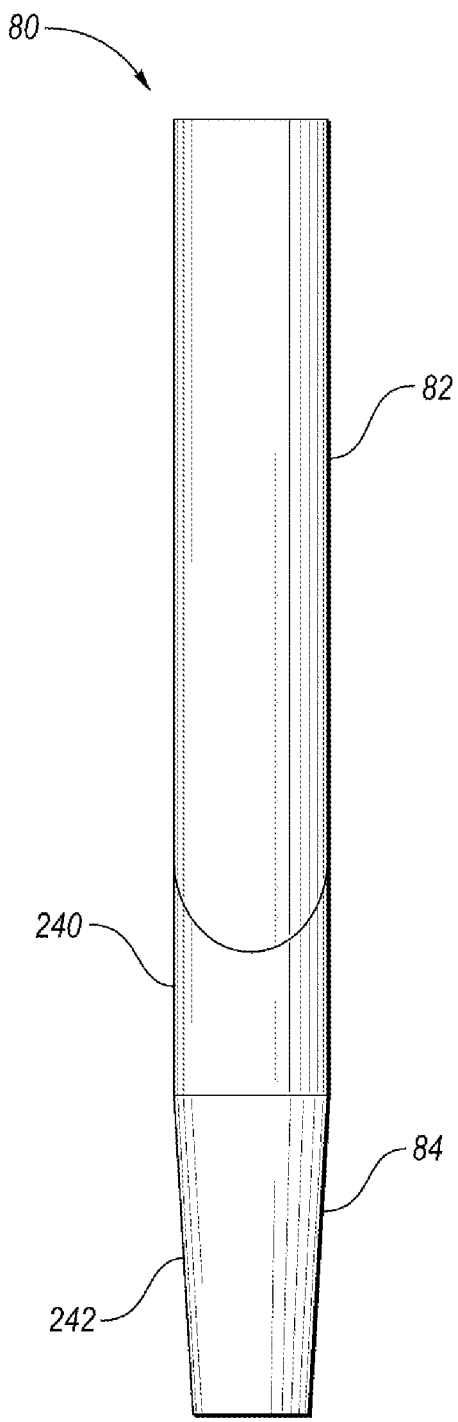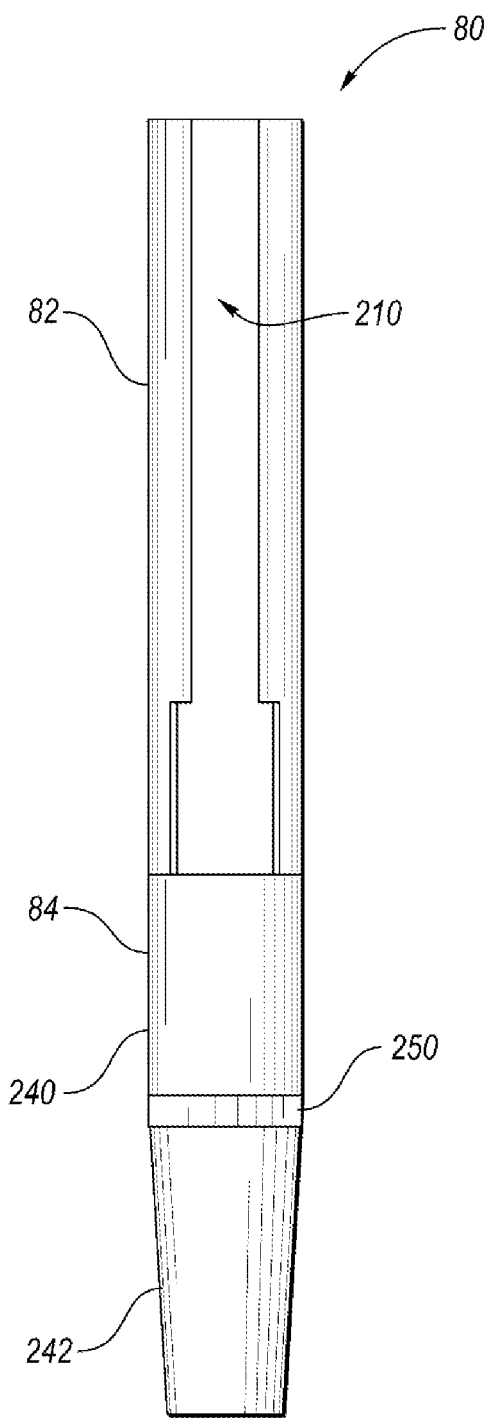
FIG. 11  FIG. 12

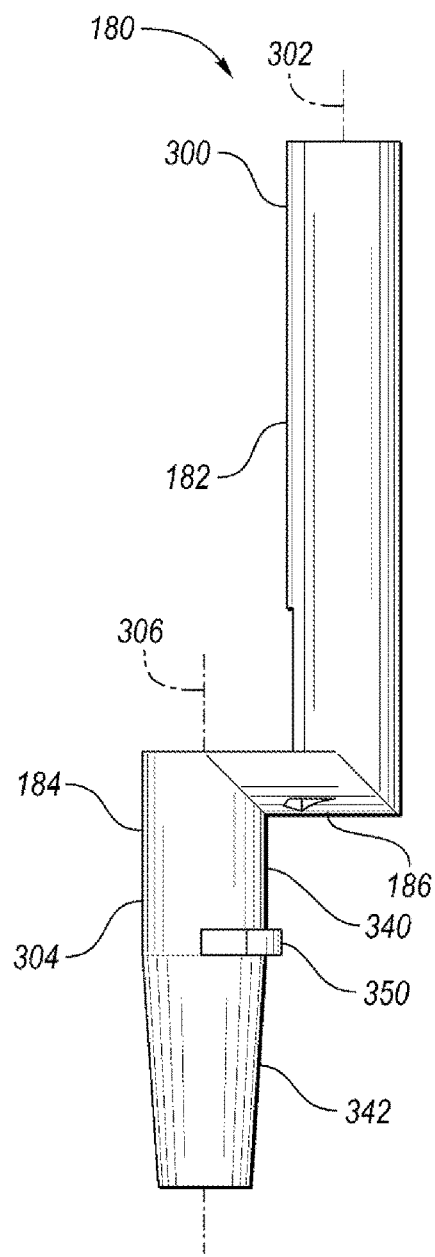 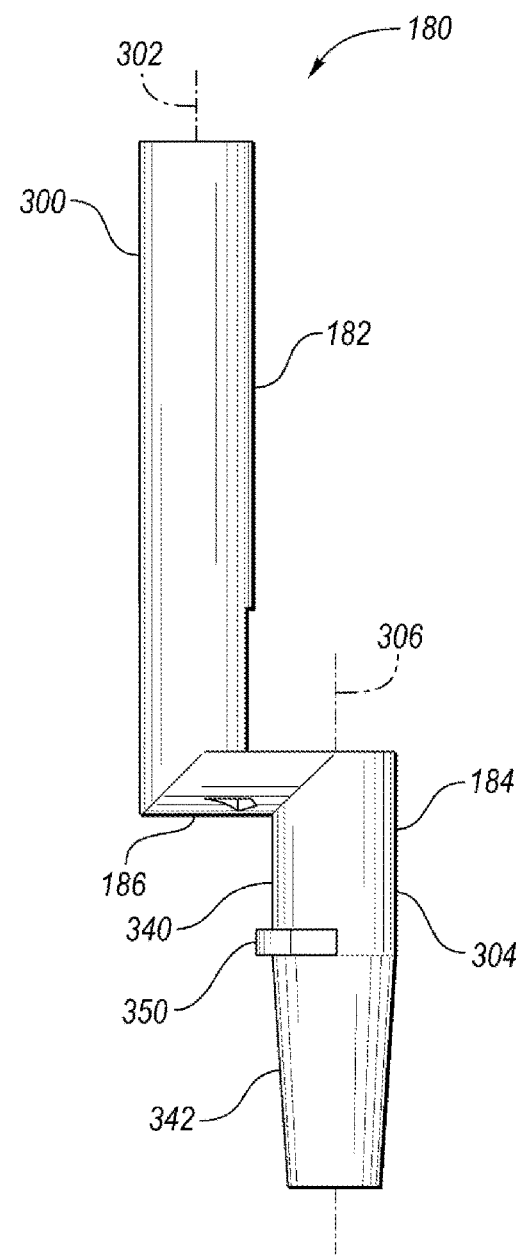
FIG. 16 FIG. 17
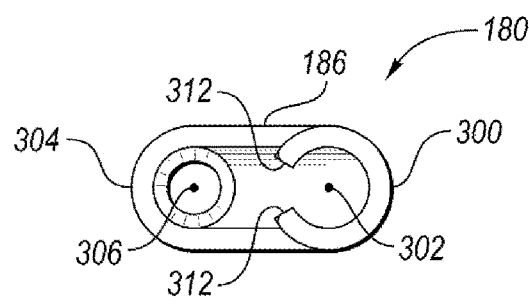 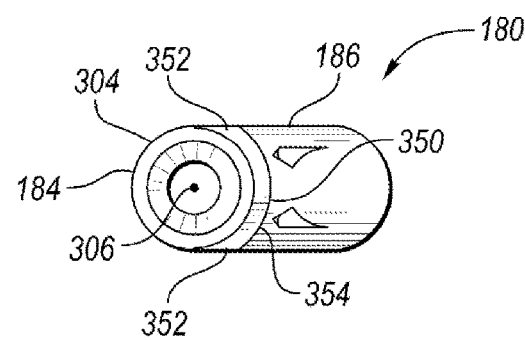
FIG. 18 FIG. 19

CONDUIT CONNECTORS AND FLUID ASSEMBLIES FOR ENTERAL FEED PUMPS, AND METHODS THEREOF

FIELD

This disclosure relates generally to pumps that are used to deliver fluids to patients, and more particularly, to conduit connectors for enteral feeding pumps.

BACKGROUND

Enteral feeding pumps are used to deliver a controlled amount of water or fluid nutrition to patients who are unable to eat, such as through a patient's nose or mouth. Example enteral feeding pumps and accessories therefor are described U.S. patent application Ser. No. 16/458,900 entitled "Feeding Set and Enteral Feeding Pump Assembly," filed Jul. 1, 2019, the contents of which are incorporated by reference in their entirety.

To advance the fluid to a patient, the pumping system may include a positive displacement pump, such as a peristaltic pump that advances the fluid through disposable tubing. The tubing sets typically connect the containers or bags of fluid to the pump and then the patient.

Enteral feeding pumps typically employ either a rotary or a linear pump. The pumps generally have a housing with a motor therein and an actuator device, such as a pump rotor, roller, or platens used to advance the fluid through the tubing. Although enteral feeding pumps are usable for a substantial amount of time, the feeding sets or tubing used with such pumps are typically changed daily.

BRIEF DESCRIPTION OF THE DRAWINGS

FIG. 11 is a left side elevation view of the feed conduit connector.

FIG. 12 is a right side elevation view of the feed conduit connector.

FIG. 16 is a front elevation view of the flush conduit connector.

FIG. 17 is a rear elevation view of the flush conduit connector.

FIG. 18 is a top plan view of the flush conduit connector.

FIG. 18 is a bottom plan view of the flush conduit connector.

DETAILED DESCRIPTION

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Described herein are fluid sets or assemblies that may be placed at least partially within an enteral feeding pump. A fluid assembly may be a "feed only" fluid assembly that includes nutritional liquid, or "flush only" fluid assembly that includes hydrating liquid. A fluid assembly includes a conduit connector sized for placement within the enteral feeding pump, and an elastomeric peristaltic tubing element fluidly connected to an exit of the conduit connector. Also described herein are methods of providing an enteral feeding pump for use with a fluid assembly, the method comprising attaching a conduit connector of the fluid assembly to a panel of the pump. The panel may be an internal panel of the pump, and the method may include opening a pump door to expose the internal panel and closing the pump door.

Figure 1:
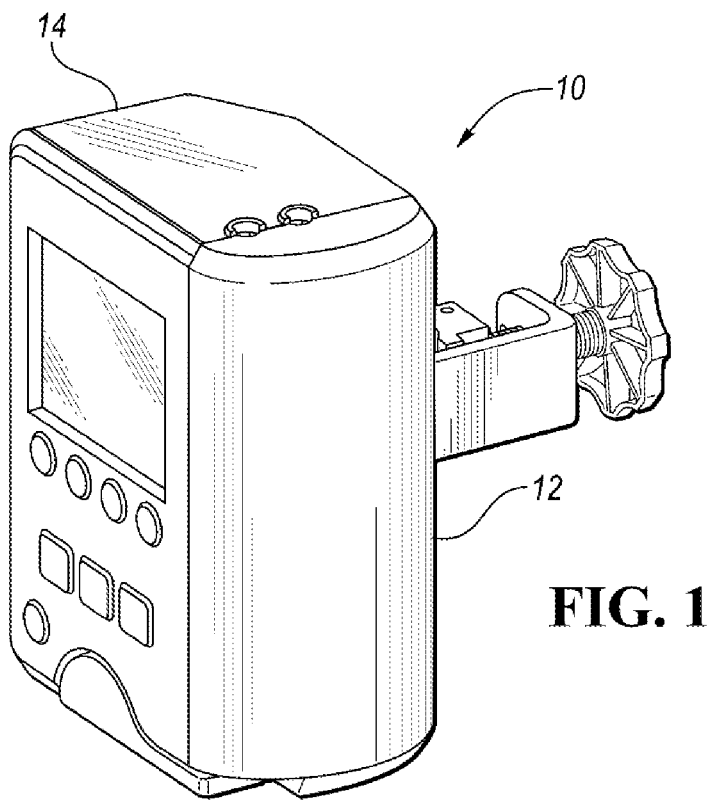
FIG. 1 is a perspective view of an enteral feeding pump.
Figure 2:
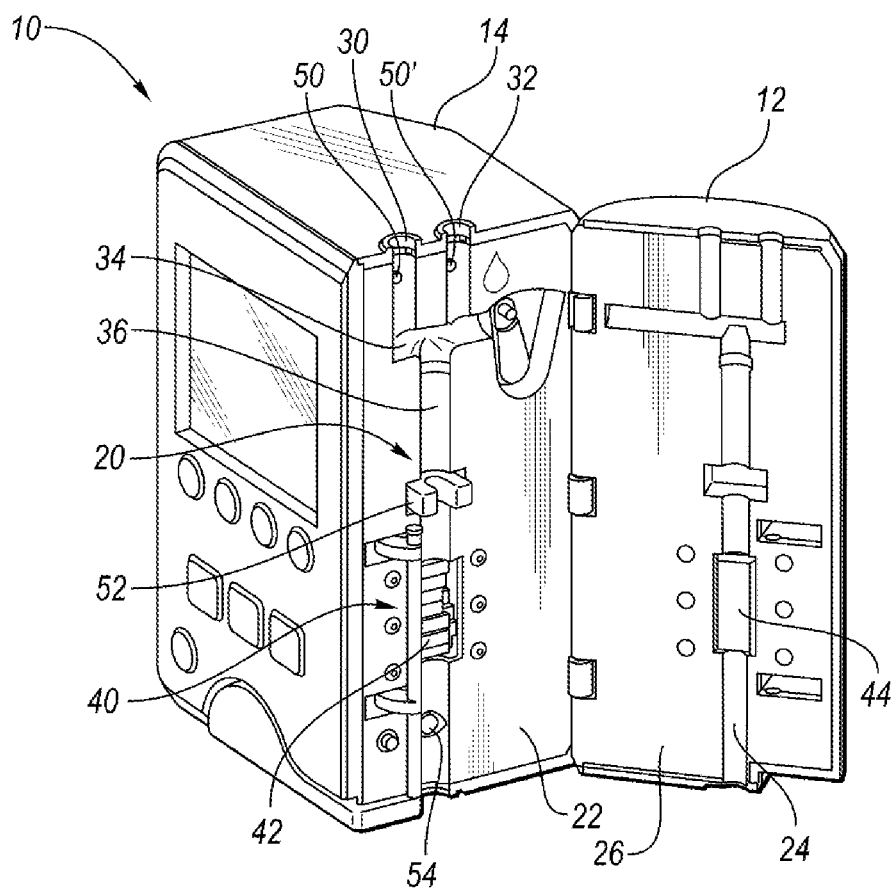
FIG. 2 is a perspective view of the enteral feeding pump with a door in an open position.

Referring now to FIGS. 1 and 2, the enteral feeding pump 10 is shown with a pump door 12 in a closed position. The enteral feeding pump 10 has a pump door 12 that is hingedly attached to a housing body 14. The pump door 12 is movable from a first position to a second position. In the first position, shown in FIG. 1, the pump door 12 is in a closed configuration and in the second position, shown in FIG. 2, the pump door 12 is in an open configuration. In the open configuration, a user may install or uninstall a fluid assembly, as discussed in greater detail below.

The enteral feeding pump 10 is configured to receive one or more fluid sets or assemblies having enteral feeding pump conduit connectors. With reference to FIG. 2, conduit connectors may be received within a depression or groove 20 formed in an internal panel 22 of the enteral feeding pump 10 and/or within a depression or groove 24 formed in an internal wall 26 of the pump door 12. The groove 20 formed in the internal panel 22 includes a first upper channel 30, a second upper channel 32, and a transverse channel 34 that extends between the first upper channel 30 and the second upper channel 32. Groove 20 also includes an elongated channel or peristaltic tube channel 36 that extends from the transverse channel 34. The channels 30, 32, 34, 36 are configured to receive tubing elements and/or conduit connectors of a fluid assembly therein, as discussed in greater detail below. The groove 24 formed in the internal wall 26 of the pump door 12 may include opposing and complementary channels for receiving tubing elements and/or conduit connectors of the fluid assembly when the pump door 12 is in the closed position.

The enteral feeding pump 10 also includes a peristaltic pump 40 proximate a groove (e.g., groove 20). The peristaltic pump 40 may be a linear peristaltic pump that includes keys 42 for pressing or pinching a peristaltic tubing element between the keys 42 and a pump surface 44 of the pump door 12 to advance the fluid therein via peristaltic action. More particularly, the keys 42 act on the peristaltic tubing element within the peristaltic tube channel 36 at right angles relative to the direction of fluid flow. Successive actuation of the keys 42 drives fluid through the peristaltic tubing. The peristaltic pump alternatively may be a rotary peristaltic pump.

The enteral feeding pump 10 may also include one or more sensors proximate the grooves 20, 24. For example, the enteral feeding pump 10 may include one or more set detection sensors 50, 50' disposed within the first upper channel 30 and/or the second upper channel 32. The set detection sensors 50, 50' are engaged or disengaged respectively when the feed or flush assembly is installed. The sensors may be push-button momentary switches that are configured to be depressed when a conduit connector of a fluid assembly is disposed in the first upper channel 30 and/or the second upper channel 32. The status of the set detection sensors 50, 50' (e.g., depressed or not depressed) may be indicative of the presence of a fluid assembly within the groove 20, as well as the type of fluid assembly received within the groove 20. For example, and as discussed in greater detail below, if set detection sensor 50 is pressed but the set detection sensor 50' is not depressed and the pump door 12 is closed, the enteral feeding pump 10 (e.g., at a processor of the enteral feeding pump 10) may determine that a "feed only" fluid assembly has been received in the groove 20. If set detection sensor 50' is depressed but the set detection sensor 50 is not depressed and the pump door 12 is closed, the enteral feeding pump 10 may determine that a "flush only" fluid assembly has been received in the groove 20. If set detection sensor 50 and set detection sensor 50' are both depressed and the pump door 12 is closed, the enteral feeding pump 10 may determine that a "feed and flush" fluid assembly has been received in the groove 20.

The enteral feeding pump 10 may also include one or both of an air sensor 52 and an occlusion sensor 54 proximate the grooves 20, 24. The air sensor 52 may be disposed within the peristaltic tube channel 36 upstream of the peristaltic pump 40. The air sensor 52 may be an ultrasonic sensor that detects air within a peristaltic tubing element. The air sensor 52 may detect a volume of air over a predetermined threshold, which may be an instantaneous air volume (e.g., a 3 millimeter air bubble) or a volume of air within a predefined period of time (e.g., 10 millimeters of air within the period of time). In response to the air sensor 52 detecting air in the peristaltic tubing element above the threshold, the enteral feeding pump 10 may stop the pumping operation of the peristaltic pump 40, and/or may output an error indicator at a user interface.

The occlusion sensor 54 may be disposed within the peristaltic tube channel 36 downstream of the peristaltic pump 40. The occlusion sensor 54 is configured to detect a deformation (e.g., "ballooning") in the peristaltic tubing element that may be indicative of an occlusion within the peristaltic tubing element (e.g., downstream from the occlusion sensor 54). In response to the occlusion sensor 54 detecting an occlusion in the peristaltic tubing element, the enteral feeding pump 10 may stop the pumping operation of the peristaltic pump 40, and/or may output an error message at the user interface.

Figure 3:
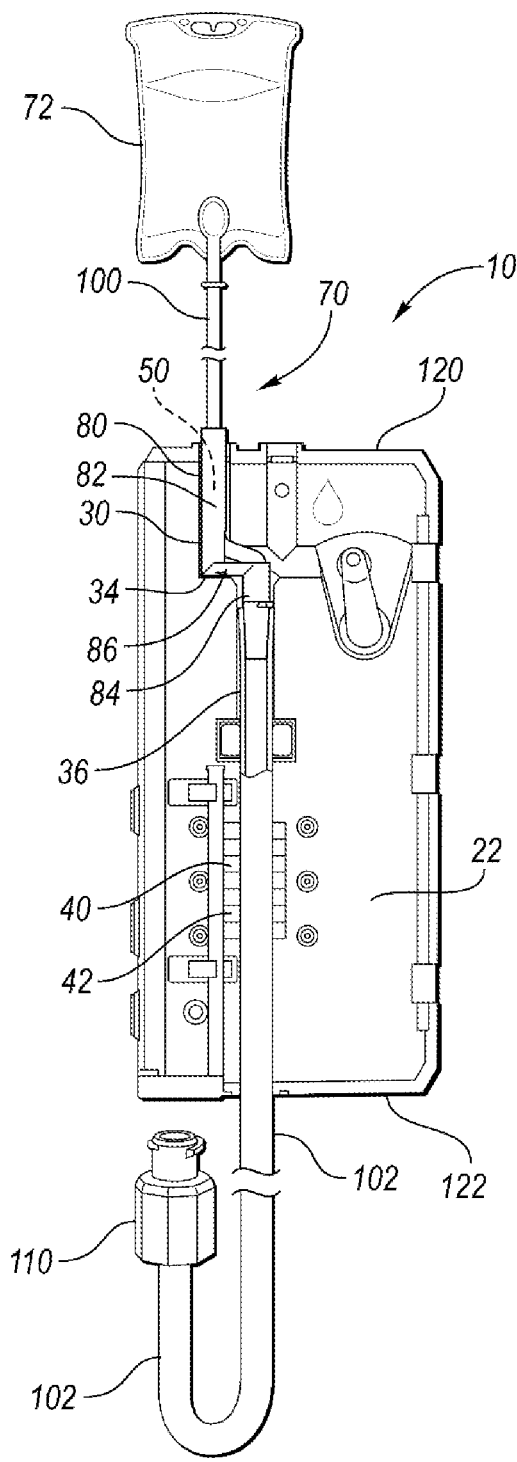
FIG. 3 is a right side elevation view of the enteral feeding pump with a clamp and the door omitted for clarity, and further showing a feed assembly installed in the enteral feeding pump.

Referring to FIG. 3, the enteral feeding pump 10 may receive a feed set or assembly 70 for connecting a first container, such as a nutrition or feed container 72 to a patient. The feed assembly 70 includes a feed conduit connector 80 having a fluid inlet portion 82, a fluid outlet portion 84, and a bridge portion 86 that extends between and connects the fluid inlet portion 82 and the fluid outlet portion 84.

The feed assembly 70 further includes a first tubing element, which may be a flexible tubing element 100 in fluidic communication with the fluid inlet portion 82. The flexible tubing element 100 may be connected at a first end to the feed container 72, and may extend at a second end opposite the first end within at least a portion of the feed conduit connector 80.

The feed assembly 70 further includes a second tubing element, which may be a peristaltic tubing element 102 in fluidic communication with the fluid outlet portion 84. The peristaltic tubing element 102 may be connected at a first end to the feed conduit connector 80 (e.g., at the fluid outlet portion 84), and is connected at a second end opposite the first end to a patient coupling 110 that permits the feed assembly 70 to be in fluid communication with a patient.

When the feed assembly 70 is installed on the internal panel 22 of the enteral feeding pump 10, the fluid inlet portion 82 is received at least partially within the first upper channel 30, the bridge portion 86 is received at least partially within the transverse channel 34, and the fluid outlet portion 84 is at least partially received in the peristaltic tubing channel 36. With the feed assembly 70 installed, the fluid inlet portion 82 is received within the first upper channel 30 such that set detection sensor 50 is depressed and set detection sensor 50' is not depressed. As noted above, this configuration of sensors 50, 50' is indicative of a "feed only" feed assembly 70 being installed within the enteral feeding pump 10.

When the feed assembly 70 is installed, the fluid inlet portion 82 may extend beyond a top edge 120 of the internal panel 22. The flexible tubing element 100 extends through the fluid in the fluid inlet portion 82, within the bridge portion 86, and within at least a portion of the fluid outlet portion 84. The peristaltic tubing element 102 is connected to the fluid outlet portion 84, and extends within the peristaltic tubing channel 36, across the keys 42 of the peristaltic pump 40, and beyond a bottom edge 122 of the internal panel 22 to the patient coupling 110. In this way, the feed container 72 is fluidly coupled to the patient coupling 110 such that fluid from the feed container 72 may be passed through the enteral feeding pump 10 to a patient.

Figure 4:
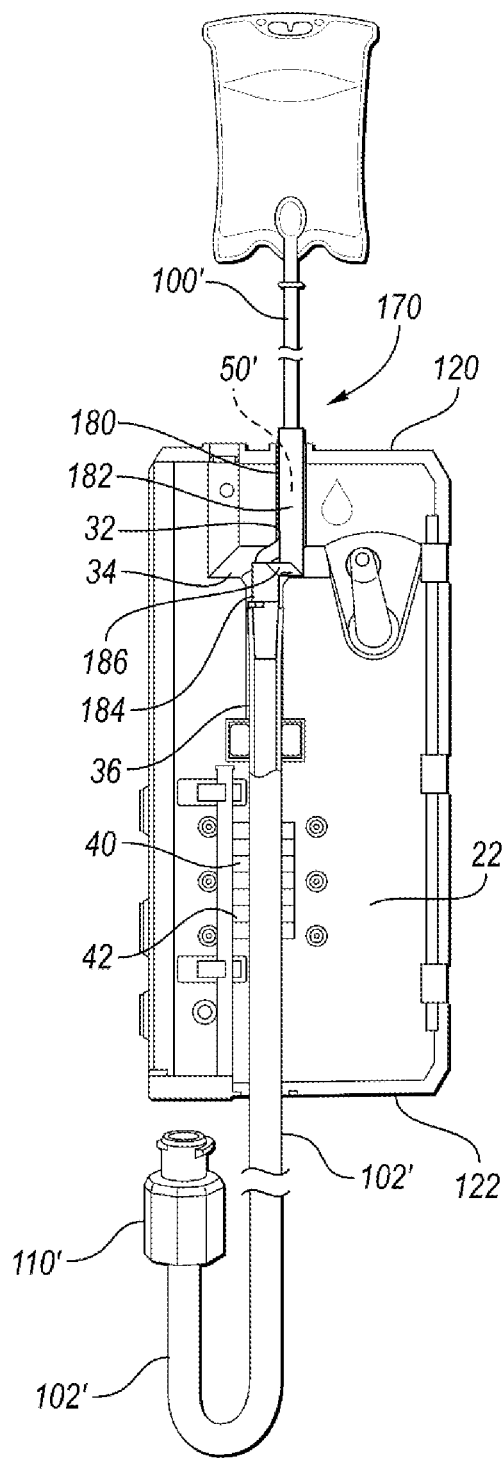
FIG. 4 is a right side elevation view of the enteral feeding pump similar to FIG. 3, and further showing a flush assembly installed in the enteral feeding pump.

Referring to FIG. 4, the enteral feeding pump 10 may receive a flush set or assembly 170 for connecting a second container, such as a hydration or flush container 172 to a patient. The flush assembly 170 includes a flush conduit connector 180 having a fluid inlet portion 182, a fluid outlet portion 184, and a bridge portion 186 that extends between and connects the fluid inlet portion 182 and the fluid outlet portion 184.

The flush assembly 170 further includes a first tubing element, which may be a flexible tubing element 100' in fluidic communication with the fluid inlet portion 182. The flexible tubing element 100' may be connected at a first end to the flush container 172, and may extend at a second end opposite the first end within at least a portion of the flush conduit connector 180.

The flush assembly 170 further includes a second tubing element, which may be a peristaltic tubing element 102' in fluidic communication with the fluid outlet portion 184. The peristaltic tubing element 102' may be connected at a first end to the flush conduit connector 180 (e.g., at the fluid outlet portion 184), and is connected at a second end opposite the first end to a patient coupling 110' that permits the flush assembly 170 to be in fluid communication with a patient.

When the flush assembly 170 is installed on the internal panel 22 of the enteral feeding pump 10, the fluid inlet portion 182 is received at least partially within the second upper channel 32, the bridge portion 186 is received at least partially within the transverse channel 34, and the fluid outlet portion 184 is at least partially received in the peristaltic tubing channel 36. With the flush assembly 170 installed, the fluid inlet portion 182 is received within the second upper channel 32 such that set detection sensor 50' is depressed and set detection sensor 50 is not depressed. As indicated above, this configuration of sensors 50, 50' is indicative of a "flush only" flush assembly 170 being installed within the enteral feeding pump 10. The cross-sectional area of the feed assembly 70 and/or flush assembly 170 at the engagement point with the sensors 50, 50' may be less than or equal to 32 mm^2. The durometer of the feed assembly 70 and/or flush assembly 170 component may be greater than or equal to 50 A.

When the flush assembly 170 is installed, the fluid inlet portion 182 may extend beyond a top edge 120 of the internal panel 22. The flexible tubing element 100' extends through the fluid in the fluid inlet portion 182, within the bridge portion 186, and within at least a portion of the fluid outlet portion 184. The peristaltic tubing element 102' is connected to the fluid outlet portion 184, and extends within the peristaltic tubing channel 36, across the keys 42 of the peristaltic pump 40, and beyond a bottom edge 122 of the internal panel 22 to the patient coupling 110'. In this way, the flush container 172 is fluidly coupled to the patient coupling 110' such that fluid from the flush container 172 may be passed through the enteral feeding pump 10 to a patient.

With reference to FIGS. 5-12, a feed conduit connector 80 includes a fluid inlet portion 82, a fluid outlet portion 84, and a bridge portion 86 that extends between and connects the fluid inlet portion 82 and the fluid outlet portion 84. The fluid inlet portion 82 extends a first longitudinal direction from the bridge portion 86, and the fluid outlet portion 84 extends a second longitudinal direction from the bridge portion 86 that is opposite the first longitudinal direction. The fluid inlet portion 82, the fluid outlet portion 84, and the bridge portion 86 may be integrally formed (e.g., injection molded) such that the feed conduit connector 80 is a unitary (i.e., one-piece) body.

The fluid inlet portion 82 and the fluid outlet portion 84 have curved wall portions that extend about axes. More particularly, the fluid inlet portion 82 includes curved wall portions 200 that extend about an inlet axis 202, and the fluid outlet portion 84 includes curved wall portions 204 that extend about an outlet axis 206. The outlet axis 206 is parallel to and laterally offset from the inlet axis 202.

Figure 5:
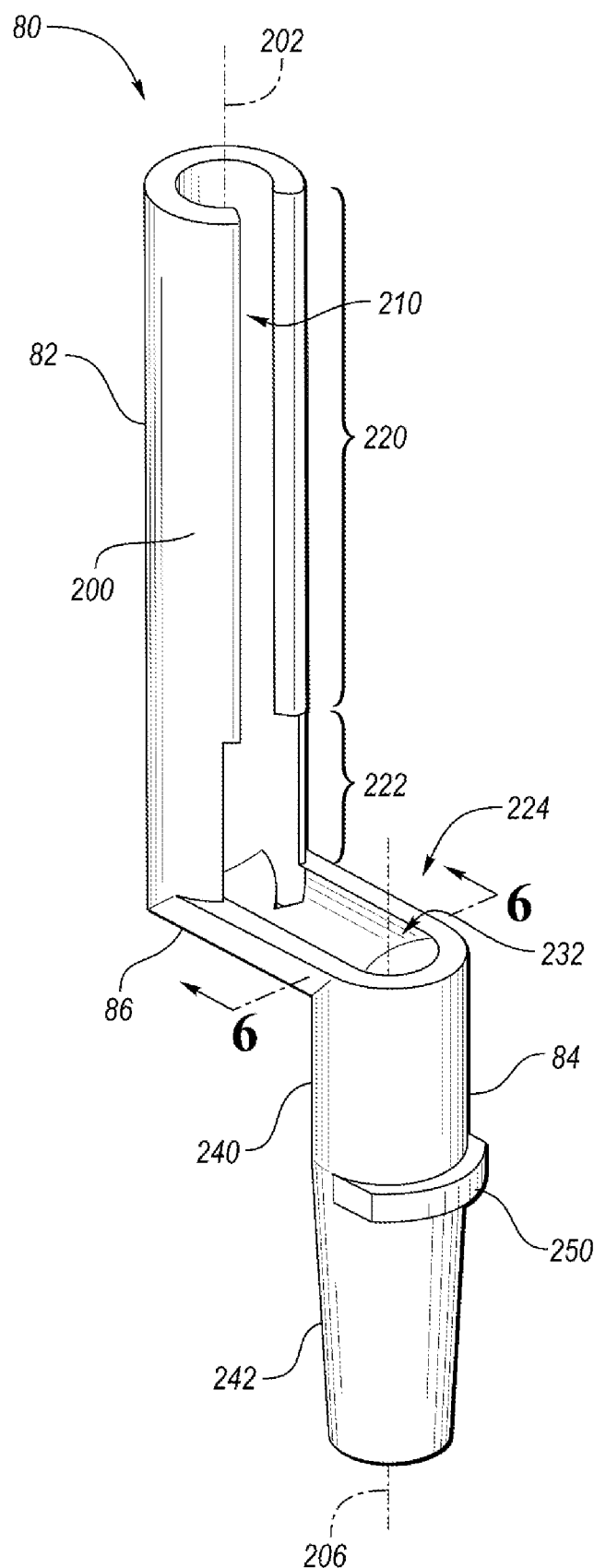
FIG. 5 is a perspective view of the feed conduit connector of the feed assembly shown in FIG. 3.
Figure 6:
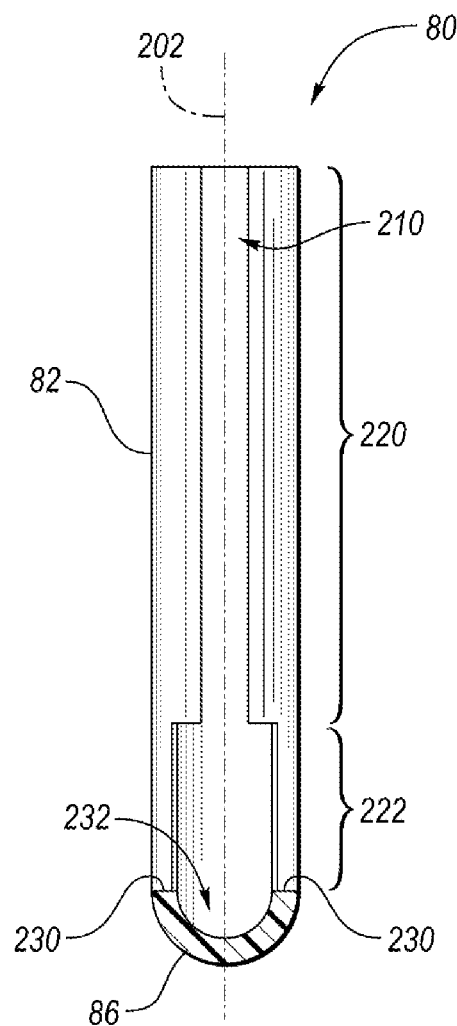
FIG. 6 is a cross section view taken along the line 6-6 of FIG. 5.
Figure 7:
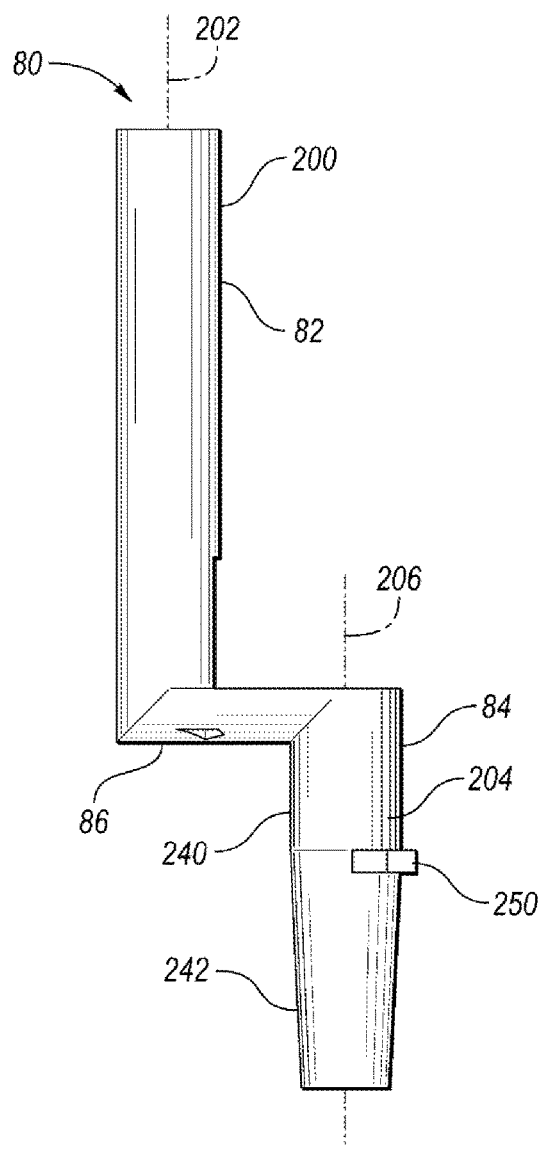
FIG. 7 is a front elevation view of the feed conduit connector.
Figure 8:
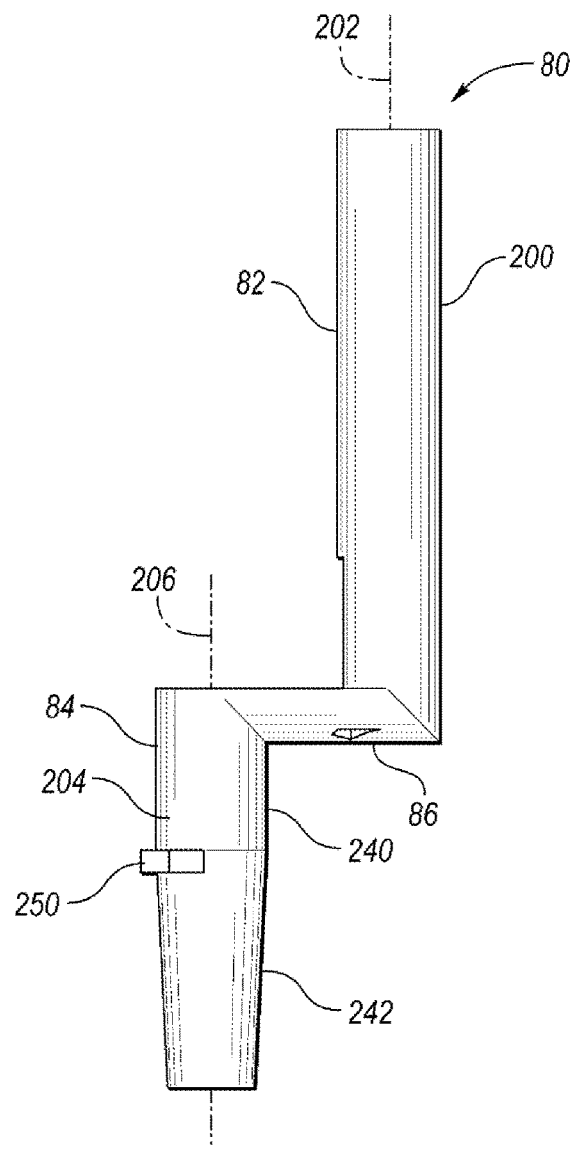
FIG. 8 is a rear elevation view of the feed conduit connector.
Figure 9:
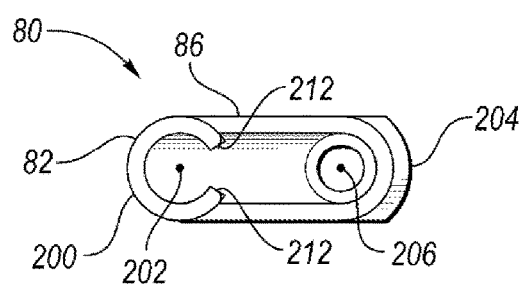
FIG. 9 is a top plan view of the feed conduit connector.

The fluid inlet portion 82 includes a slot 210 for receiving tubing through the slot 210. More particularly, the curved wall portions 200 of the fluid inlet portion 82 define an elongated side slot 210 that extends parallel to the inlet axis 202. The elongated side slot 210 may extend along substantially an entire longitudinal length of the fluid inlet portion 82. In one approach, the curved wall portions 200 have opposing tube-receiving longitudinal ends 212, as shown in FIG. 9, such that the fluid inlet portion 82 has a generally C-shaped cross section in a plane orthogonal to the inlet axis 202. Referring to FIGS. 5 and 6, the fluid inlet portion 82 may include an upper wall region 220 that extends angularly a first degree about the inlet axis 202, and a lower wall region 222 that extends angularly a second degree that is different than (e.g., less than) the first degree about the inlet axis 202. In this way, and as discussed in greater detail below, the upper wall region 220 may form a tube retaining region, and the lower wall region 222 may form at least part of a cutout or relief region 224. The relief region 224 permits the tubing to transition gradually between the fluid inlet portion 82 and the fluid outlet portion 84.

The bridge portion 86 extends between and connects the fluid inlet portion 82 and the fluid outlet portion 84. In one approach, the bridge portion 86 extends generally orthogonal to the inlet axis 202 and/or the outlet axis 206. As shown in FIG. 6, the bridge portion 86 has a generally U-shaped cross section. In this way, end portions 230 of the generally U-shaped cross section may define an upper bridge slot 232. The upper bridge slot 232 and the lower wall region 222 cooperate to form at least part of the relief region 224.

The fluid outlet portion 84 includes a generally cylindrical portion 240 that extends from the bridge portion 86, and a generally frustoconical portion 242 that extends from the generally cylindrical portion 240. The generally frustoconical portion 242 may be sized to receive a tubing element such as peristaltic tubing element 102 about an outer surface of the generally frustoconical portion 242.

Figure 10:
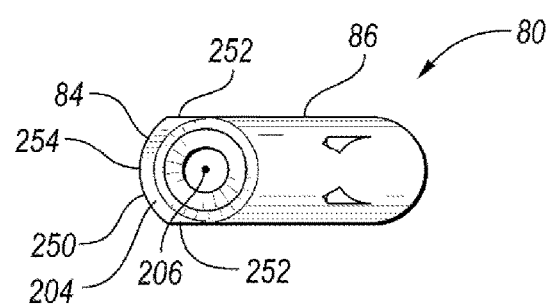
FIG. 10 is a bottom plan view of the feed conduit connector.

The fluid outlet portion 84 further includes a stop member 250 that protrudes from an exterior surface of the curved wall portion 204 the fluid outlet portion 84. In one approach, the stop member 250 protrudes in a generally lateral direction opposite the fluid inlet portion 82. Referring to FIG. 10, the stop member 250 may include side walls 252 that extend generally parallel to the bridge portion 86, and a curved wall 254 that extends between the side walls 252. The stop member 250 may be disposed at the intersection of the generally cylindrical portion 240 and the generally frustoconical portion 242. In this way, the stop member 250 may limit longitudinal travel of a tubing element (e.g., peristaltic tubing element 102) that is received about an outer surface of the fluid outlet portion 84.

Figure 13:
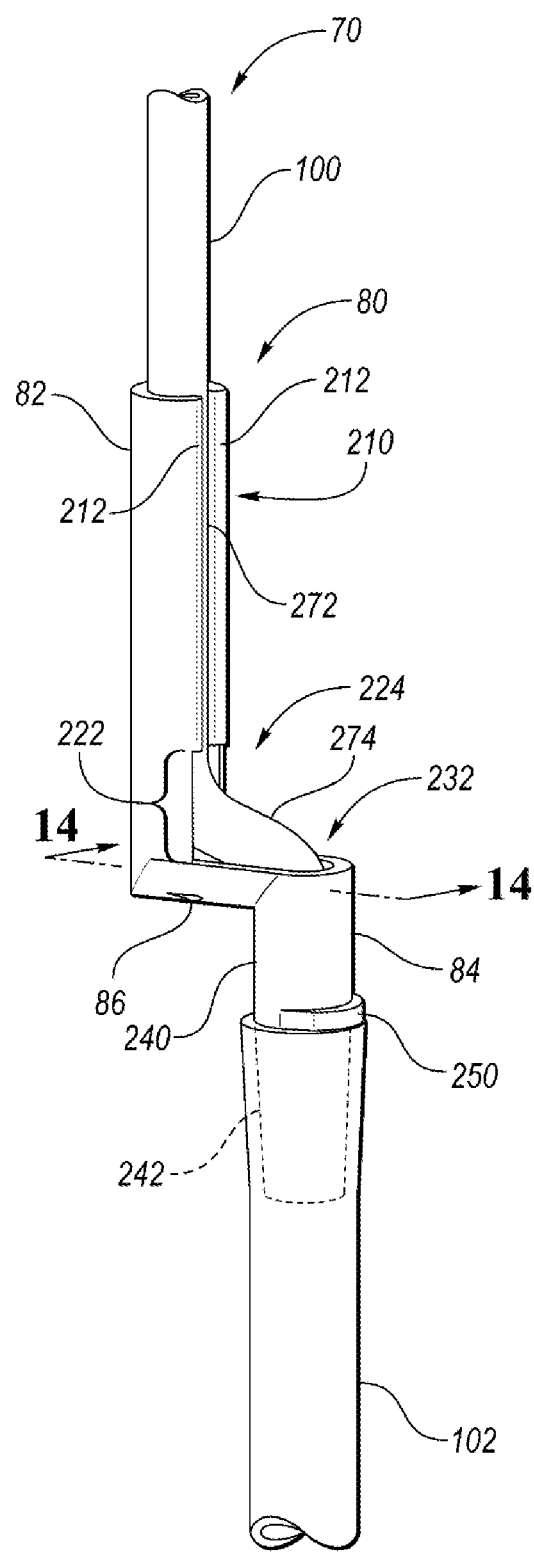
FIG. 13 is a perspective view of a portion of the feed assembly depicted in FIG. 3.
Figure 14:
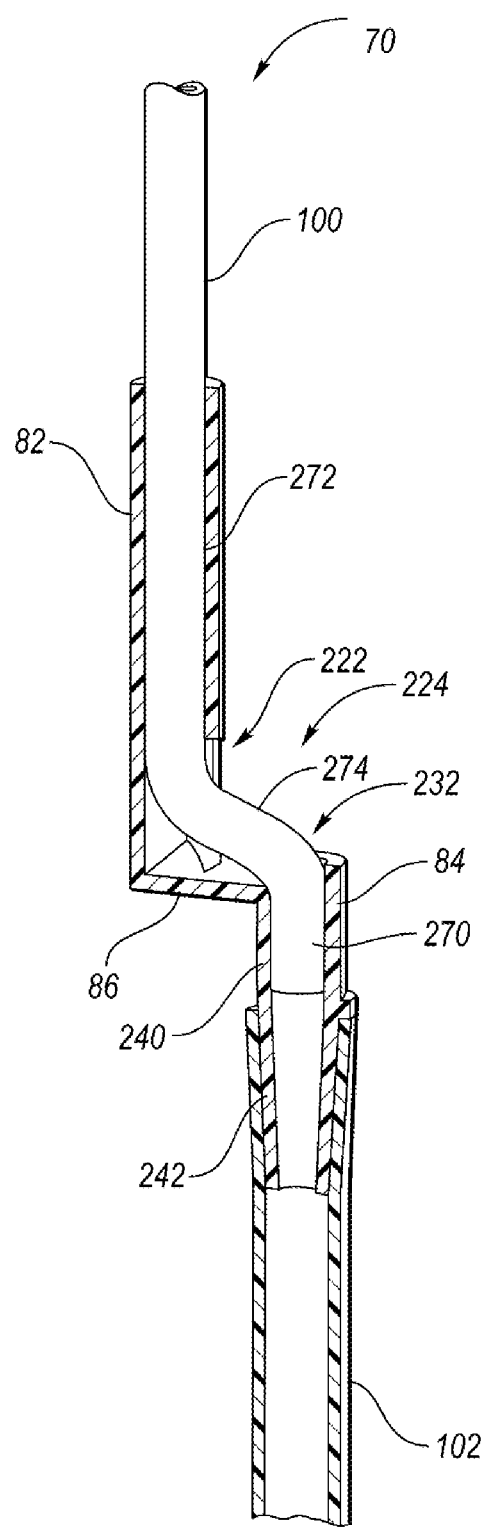
FIG. 14 is a cross section view taken along the line 14-14 of FIG. 13.

Referring to FIGS. 13 and 14, a feed assembly 70 may be assembled by inserting an end portion 270 of a flexible tubing element 100 through the upper bridge slot 232 and into the fluid outlet portion 84 (e.g., into the generally cylindrical portion 240). The end portion 270 may be secured to an internal wall of the fluid outlet portion 84. For example, the end portion 270 may be press-fit, glued, or fastened to the internal wall of the fluid outlet portion 84.

A body portion 272 of the flexible tubing element 100 may then be moved into the fluid inlet portion 82. For example, the body portion 272 may be laterally passed between the opposing tube-receiving longitudinal ends 212 of the curved wall portion 200 of the fluid inlet portion 82. The curved wall portion 200 may be made of a material is sufficiently flexible to the curved wall portion 200 to flex to allow passage of the body portion 272 between the opposing tube-receiving longitudinal ends 212, while sufficiently resilient to return to original position upon receiving the body portion 272 within the fluid inlet portion 82. In the original position, the curved wall portion 200 retains the body portion 272 of the flexible tubing element 100 to inhibit movement of the body portion 272 radially away from the inlet axis 202.

When the end portion 270 of the flexible tubing element 100 is secured within the fluid outlet portion 84 and the body portion 272 is retained within fluid inlet portion 82, the flexible tubing element 100 forms a curved transition portion 274 between the end portion 270 and the body portion 272. The curved transition portion 274 protrudes through the relief region 224. For example, the curved transition portion 274 extends away from the fluid inlet portion 82 and through the lower wall region 222 of the slot 210 of the fluid inlet portion 82. The curved transition portion 274 further extends across the bridge portion 86 at least partially through the upper bridge slot 232. The flexible tubing element 100 may be spaced apart from at least part of the bridge portion 86 at the curved transition portion 274. The curved transition portion 274 further curves into the fluid outlet portion 84 to be at least partially received internally within the fluid outlet portion 84. In this way, the curved transition portion 274 may form a generally S-shaped curved transition portion.

With reference to FIGS. 15-21, a flush conduit connector 180 includes a fluid inlet portion 182, a fluid outlet portion 184, and a bridge portion 186 that extends between and connects the fluid inlet portion 182 and the fluid outlet portion 184. The fluid inlet portion 182 extends a first longitudinal direction from the bridge portion 186, and the fluid outlet portion 184 extends a second longitudinal direction from the bridge portion 186 that is opposite the first longitudinal direction. The fluid inlet portion 182, the fluid outlet portion 184, and the bridge portion 186 may be integrally formed (e.g., injection molded) such that the flush conduit connector 180 is a unitary (i.e., one-piece) body.

The fluid inlet portion 182 and the fluid outlet portion 184 have curved wall portions that extend about axes. More particularly, the fluid inlet portion 182 includes curved wall portions 300 that extend about an inlet axis 302, and the fluid outlet portion 184 includes curved wall portions 304 that extend about an outlet axis 306. The outlet axis 306 is parallel to and laterally offset from the inlet axis 302.

Figure 15:
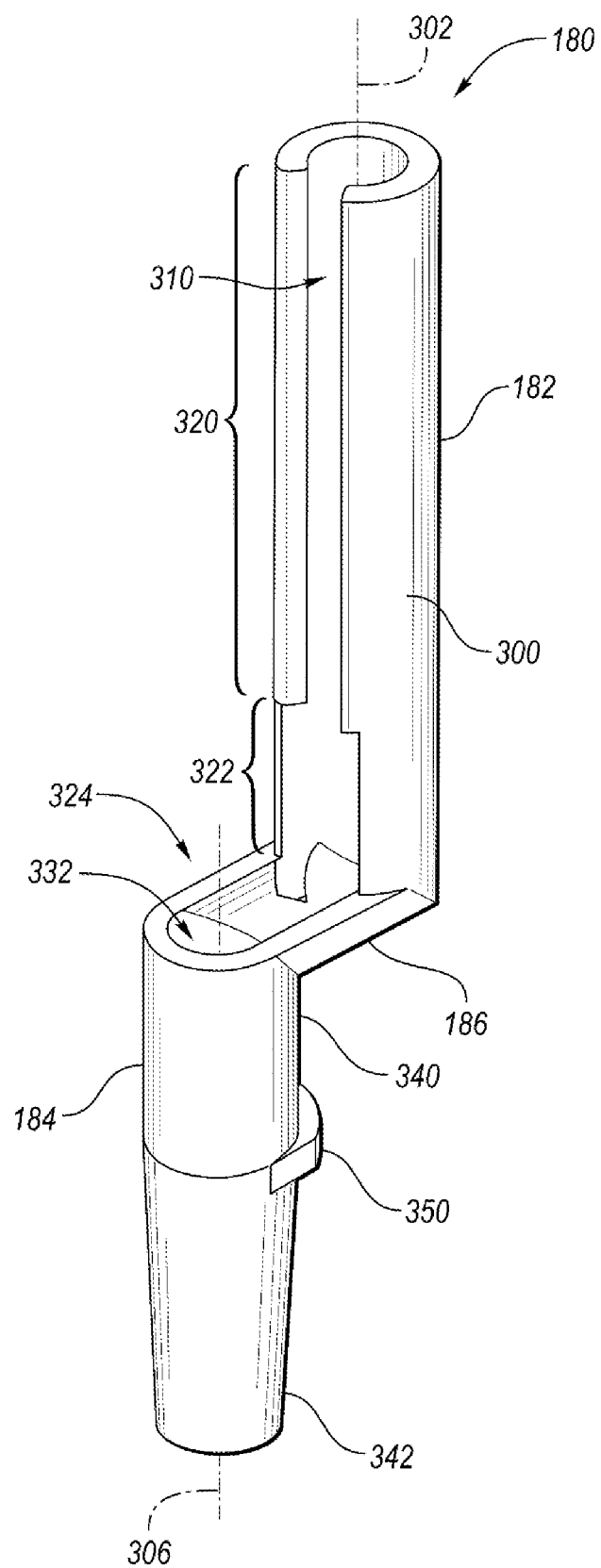
FIG. 15 is a perspective view of the flush conduit connector of the flush assembly shown in FIG. 4.
Figure 20:
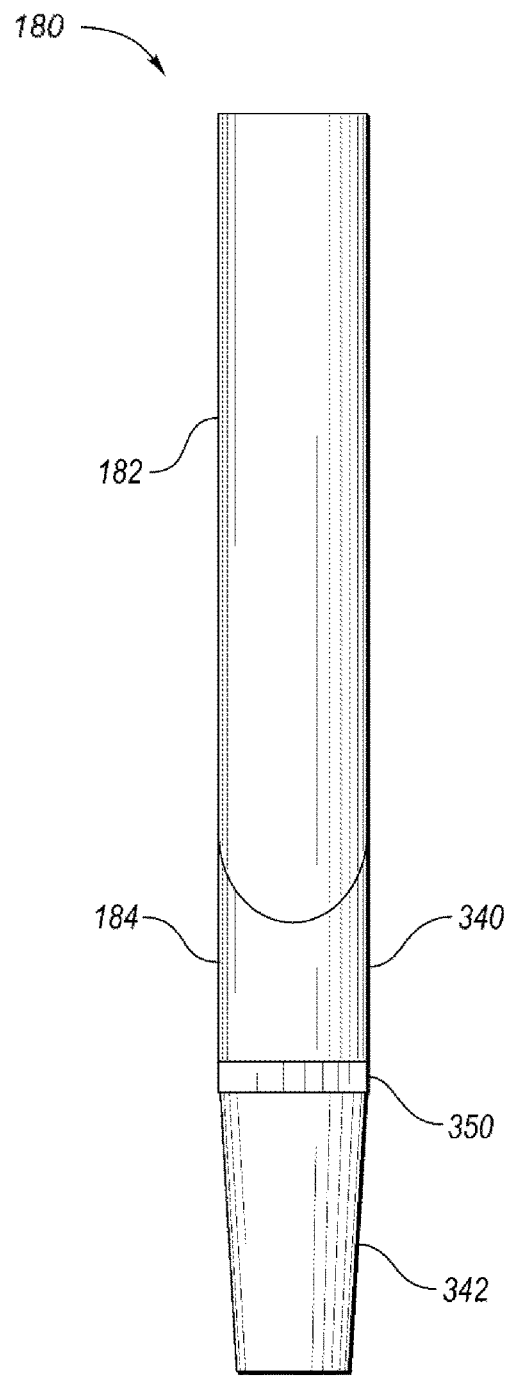
FIG. 20 is a left side elevation view of the flush conduit connector.
Figure 21:
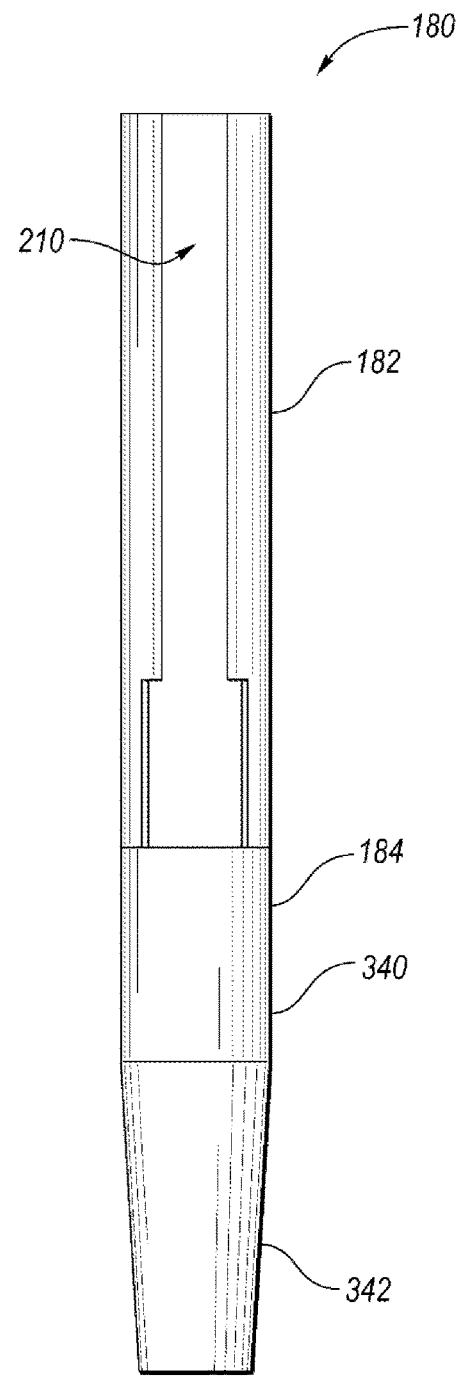
FIG. 21 is a right side elevation view of the flush conduit connector.

The fluid inlet portion 182 includes a slot 310 for receiving tubing through the slot 310. More particularly, the curved wall portions 300 of the fluid inlet portion 182 define an elongated side slot 310 that extends parallel to the inlet axis 302. The elongated side slot 310 may extend along substantially an entire longitudinal length of the fluid inlet portion 182. In one approach, the curved wall portions 300 have opposing tube-receiving longitudinal ends 312, as shown in FIG. 18, such that the fluid inlet portion 182 has a generally C-shaped cross section in a plane orthogonal to the inlet axis 302. Referring to FIG. 15, the fluid inlet portion 182 may include an upper wall region 320 that extends angularly a first degree about the inlet axis 302, and a lower wall region 322 that extends angularly a second degree that is different than (e.g., less than) the first degree about the inlet axis 302. In this way, and as discussed in greater detail below, the upper wall region 320 may form a tube retaining region, and the lower wall region 322 may form at least part of a relief region 324.

The bridge portion 186 extends between and connects the fluid inlet portion 182 and the fluid outlet portion 184. In one approach, the bridge portion 186 extends generally orthogonal to the inlet axis 302 and/or the outlet axis 306. Similar to the bridge portion 86 shown in FIG. 6, the bridge portion 186 has a generally U-shaped cross section. In this way, end portions 330 of the generally U-shaped cross section may define an upper bridge slot 332. The upper bridge slot 332 and the lower wall region 322 cooperate to form at least part of the cutout or relief region 324.

The fluid outlet portion 184 includes a generally cylindrical portion 340 that extends from the bridge portion 186, and a generally frustoconical portion 342 that extends from the generally cylindrical portion 340. The generally frustoconical portion 342 may be sized to receive a tubing element such as peristaltic tubing element 102 about an outer surface of the generally frustoconical portion 342.

The fluid outlet portion 184 further includes a stop member 350 that protrudes from an exterior surface of the curved wall portion 304 the fluid outlet portion 184. In one approach, the stop member 350 protrudes in a generally lateral direction toward the fluid inlet portion 182. Referring to FIG. 19, the stop member 350 may include side walls 352 that extend generally parallel to the bridge portion 186, and a curved wall 354 that extends between the side walls 352. The stop member 350 may be disposed at the intersection of the generally cylindrical portion 340 and the generally frustoconical portion 342. In this way, the stop member 350 may limit longitudinal travel of a tubing element (e.g., peristaltic tubing element 102) that is received about an outer surface of the fluid outlet portion 184.

The flush conduit connector 180 may receive tubing (e.g., flexible tubing element 100 and peristaltic tubing element 102) in a similar manner as the feed conduit connector discussed above.

In one approach, a method of assembling a fluid assembly includes inserting a first end (e.g., end portion 270 of FIG. 14) of a flexible tubing element 100 into a fluid outlet portion 84, 184 of a conduit connector 80, 180. The method may further include laterally passing a body portion 272 of the flexible tubing element 100 through an elongated side slot 210, 310 of a fluid inlet portion 82, 182 of the conduit connector 80, 180 to secure the flexible tubing element 100 within the fluid inlet portion 82, 182. The method may further include securing a peristaltic tubing element 102 to an outer surface of the fluid outlet portion 84, 184. As discussed, the fluid inlet portion 82, 182 and the fluid outlet portion 84, 184 may be parallel and laterally offset by a bridge portion 86, 186 that extends between the fluid inlet portion 82, 182 and the fluid outlet portion 84, 184.

Laterally passing the body portion 272 of the flexible tubing element 100 through the elongated side slot 210, 310 of the fluid inlet portion 82, 182 of the conduit connector 80, 180 may include bending the flexible tubing element proximate the bridge portion 86, 186 to form a curved transition portion 274 of the flexible tubing element 100. At least a portion of the curved transition portion 274 of the flexible tubing element 100 may be spaced apart from the bridge portion 86, 186, and may protrude through a relief region 224, 324 of the conduit connector 80, 180.

A method of installing a fluid assembly, such as feed assembly 70 or flush assembly 170, at an enteral feed pump 10 includes inserting a conduit connector 80, 180 of the fluid assembly at an internal panel 22 of the enteral feeding pump 10. The method may further include inserting a peristaltic tubing element 102 of the fluid assembly within a peristaltic tube channel 36 of the internal panel 22. As discussed, the internal panel 22 may include at least two set detection sensors (e.g., sensors 50, 50') that are configured to be pressed upon disposing the fluid assembly at the internal panel 22. In one approach, disposing the fluid assembly at the internal panel depresses a first detection sensors (e.g., sensor 50 or sensor 50') and not a second detection sensor (e.g., the other of sensor 50 or sensor 50'). In this way, the enteral feeding pump 10 (e.g., at a processor of the enteral feeding pump 10) may determine that a "feed only" fluid assembly has been received at the internal panel 22, or that a "flush only" fluid assembly has been received at the internal panel 22.

All methods described herein can be performed in any suitable order unless otherwise indicated herein or otherwise clearly contradicted by context. The use of any examples or exemplary language is intended to be exemplary and not to pose a limitation on the scope of the claims. Any statement herein as to the nature or benefits of the invention or of the preferred embodiments is not intended to be limiting. The claims are intended to cover all modifications and equivalents as permitted by applicable law. Any combination of the above-described elements in all possible variations thereof is encompassed by the invention unless otherwise indicated herein or otherwise clearly contradicted by context. The identification herein of any reference or patent, even if identified as "prior," is not intended to constitute a concession that such reference or patent is available as prior art against the present invention. The identification of any patent is not intended as a concession that the claims of such patent cover any of the heretofore-described embodiments. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. An enteral feeding pump conduit connector comprising:
   a fluid inlet portion having an inlet axis;
   a fluid outlet portion having an outlet axis that is parallel to and laterally offset from the inlet axis; and
   a bridge portion extending between and connecting the fluid inlet portion and the fluid outlet portion,
   wherein the fluid inlet portion defines an elongated side slot extending parallel to the inlet axis for receiving tubing through the elongated side slot.

2. The conduit connector of claim 1 wherein the fluid inlet portion includes an upper wall region that extends angularly a first degree about the inlet axis and a lower wall region that extends angularly a second degree about the inlet axis, the first degree greater than the second degree.

3. The conduit connector of claim 1 wherein the bridge portion has a generally U-shaped cross section, wherein end portions of the generally U-shaped cross section define an upper bridge slot.

4. The conduit connector of claim 1 wherein the fluid inlet portion extends a first longitudinal direction from the bridge portion, and wherein the fluid outlet portion extends a second longitudinal direction from the bridge portion that is opposite the first longitudinal direction.

5. The conduit connector of claim 1 wherein the fluid outlet portion includes a stop member protruding from an exterior surface of the fluid outlet portion.

6. The conduit connector of claim 5 wherein the stop member protrudes in a generally lateral direction opposite the fluid inlet portion.

7. The conduit connector of claim 5 wherein the stop member protrudes in a generally lateral direction toward the fluid inlet portion.

8. An enteral feeding pump conduit connector comprising:
   a bridge portion;
   a fluid inlet portion extending from a first end portion of the bridge in a first direction; and
   a fluid outlet portion extending from a second end portion of the bridge opposite the first end portion in a second direction opposite the first direction;
   wherein the conduit connector includes a relief region proximate the bridge portion.

9. The enteral feeding pump conduit connector of claim 8 wherein the fluid inlet portion forms a first relief portion in a fluid inlet wall, wherein the bridge portion forms a second relief portion in a bridge wall, the first and second relief portions cooperating to at least partially form the relief region.

10. A fluid assembly comprising:
    an enteral feeding pump conduit connector including
    a fluid inlet portion having an inlet axis,
    a fluid outlet portion having an outlet axis that is parallel to and laterally offset from the inlet axis, and
    a bridge portion extending between and connecting the fluid inlet portion and the fluid outlet portion,
    wherein the fluid inlet portion defines an elongated side slot extending parallel to the inlet axis for receiving tubing through the elongated side slot;
    a flexible tubing element in fluidic communication with the fluid inlet portion; and
    a peristaltic tubing element in fluidic communication with the fluid outlet portion.

11. The fluid assembly of claim 10 wherein the flexible tubing element extends through the fluid inlet portion, across the bridge portion, and is at least partially received internally within the fluid outlet portion.

12. A fluid assembly for use with an enteral feeding pump, the fluid assembly comprising:
    a conduit connector including
    a bridge portion,
    a fluid inlet portion extending from a first end portion of the bridge in a first direction, and
    a fluid outlet portion extending from a second end portion of the bridge opposite the first end portion in a second direction opposite the first direction,
    wherein the conduit connector includes a relief region proximate the bridge portion;
    a flexible tubing element extending through the fluid inlet portion and to the fluid outlet portion for connecting the conduit connector with a bag of fluid, the flexible tubing element forming a curved transition portion that protrudes through the relief region; and
    a peristaltic tubing element secured to the fluid outlet portion.

13. The fluid assembly of claim 12 wherein the flexible tubing element is spaced apart from at least part of the bridge portion at the curved transition portion.

14. The fluid assembly of claim 12 wherein the fluid inlet portion defines an elongated side slot extending for laterally receiving the flexible tubing element therethrough.

15. The fluid assembly of claim 12 wherein the flexible tubing element extends into the fluid outlet portion and is secured to an internal wall of the fluid outlet portion.

16. The fluid assembly of claim 12 wherein the peristaltic tubing element is secured to an outer surface of the fluid outlet portion.

17. A method of assembling a fluid assembly comprising:
inserting a first end of a flexible tubing element into a fluid outlet portion of a conduit connector;
laterally passing a body of the flexible tubing element through an elongated side slot of a fluid inlet portion of the conduit connector to secure the flexible tubing element within the fluid inlet portion; and
securing a peristaltic tubing element to an outer surface of the fluid outlet portion and wherein the fluid inlet portion and the fluid outlet portion are parallel and laterally offset by a bridge portion that extends between the fluid inlet portion and the fluid outlet portion.

18. The method of claim 17 wherein laterally passing the body of the flexible tubing element through the elongated side slot of the fluid inlet portion of the conduit connector includes bending the flexible tubing element proximate the bridge portion to form a curved transition portion of the flexible tubing element.

19. The method of claim 18 wherein at least a portion of the curved transition portion of the flexible tubing element is spaced apart from the bridge portion and protrudes through a relief region of the conduit connector.

20. A method of installing a fluid assembly at an enteral feed pump, the method comprising:
inserting a conduit connector of the fluid assembly at an internal panel of the enteral feeding pump, the conduit connector having a bridge portion, a fluid inlet portion extending from a first end portion of the bridge in a first direction, and a fluid outlet portion extending from a second end portion of the bridge opposite the first end portion in a second direction opposite the first direction, wherein the conduit connector includes a relief region proximate the bridge portion, and wherein a flexible tubing element of the fluid assembly protrudes through the relief region; and
inserting a peristaltic tubing element of the fluid assembly that is secured to the fluid outlet portion within a channel of the internal panel.

21. The method of claim 20 wherein the enteral feeding pump includes at least two set detection sensors configured to be engaged upon disposing the fluid assembly at the internal panel, wherein disposing the fluid assembly at the internal panel engages a first detection sensor and not a second detection sensor of the at least two set detection sensors.

\* \* \* \* \*